(12) United States Patent
Jesmanowicz et al.

(10) Patent No.: US 9,414,766 B2
(45) Date of Patent: Aug. 16, 2016

(54) METHOD FOR SIMULTANEOUS MULTI-SLICE MAGNETIC RESONANCE IMAGING USING SINGLE AND MULTIPLE CHANNEL RECEIVER COILS

(75) Inventors: Andrzej Jesmanowicz, Brookfield, WI (US); Shi-Jiang Li, Brookfield, WI (US); James S. Hyde, Dousman, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 849 days.

(21) Appl. No.: 13/581,209

(22) PCT Filed: Feb. 25, 2011

(86) PCT No.: PCT/US2011/026250
§ 371 (c)(1),
(2), (4) Date: Aug. 24, 2012

(87) PCT Pub. No.: WO2011/106649
PCT Pub. Date: Sep. 1, 2011

(65) Prior Publication Data
US 2012/0319686 A1    Dec. 20, 2012

Related U.S. Application Data

(60) Provisional application No. 61/308,170, filed on Feb. 25, 2010.

(51) Int. Cl.
*G01R 33/56* (2006.01)
*A61B 5/055* (2006.01)
(Continued)

(52) U.S. Cl.
CPC .............. *A61B 5/055* (2013.01); *G01R 33/446* (2013.01); *G01R 33/56545* (2013.01);
(Continued)

(58) Field of Classification Search
CPC .............. G01R 33/4806; G01R 33/446; G01R 33/4835; G01R 33/5611; G01R 33/5616; G01R 33/56545; G01R 33/56563; G01R 33/4836; A61B 5/055; A61B 5/7257
USPC .......................... 324/300–322; 382/131–132
See application file for complete search history.

(56) References Cited

U.S. PATENT DOCUMENTS

2005/0096534 A1* 5/2005 Zhu et al. ...................... 600/422
2006/0261810 A1* 11/2006 Fautz et al. ................... 324/309
(Continued)

OTHER PUBLICATIONS

Breuer, F. A., Blaimer, M., Mueller, M. F., Seiberlich, N., Heidemann, R. M., Griswold, M. A. and Jakob, P. M. (2006), Controlled aliasing in volumetric parallel imaging (2D CAIPIRINHA). Magn Reson Med, 55: 549-556. doi: 10.1002/mrm.20787.*

(Continued)

*Primary Examiner* — Melissa Koval
*Assistant Examiner* — Rishi Patel
(74) *Attorney, Agent, or Firm* — Quarles & Brady LLP

(57) ABSTRACT

A method for reconstructing a plurality of images depicting a subject from image data that is simultaneously acquired from a corresponding plurality of slice locations with a magnetic resonance imaging (MRI) system is provided. Image data is acquired following the application of radio frequency (RF) energy to the plurality of slice locations. The RF energy is tailored to provide a different phase to each of the plurality of slice locations. Reference image data is also acquired for each slice location following the application of RF energy that has the same phase as is used to excite the respective slice location for the acquisition of the image data. Aliased images are reconstructed from the image data, and reference images are reconstructed from the reference image data. Using both of these image sets, an unaliased image is produced for each of the plurality of slice locations.

21 Claims, 9 Drawing Sheets

(51) Int. Cl.
*G01R 33/44* (2006.01)
*G01R 33/565* (2006.01)
*A61B 5/00* (2006.01)
*G01R 33/48* (2006.01)
*G01R 33/483* (2006.01)
*G01R 33/561* (2006.01)

(52) U.S. Cl.
CPC .......... *A61B 5/7257* (2013.01); *G01R 33/4806* (2013.01); *G01R 33/4835* (2013.01); *G01R 33/5611* (2013.01); *G01R 33/5616* (2013.01); *G01R 33/56563* (2013.01)

(56) References Cited

U.S. PATENT DOCUMENTS

| 2009/0072827 | A1* | 3/2009 | Hargreaves | 324/309 |
| 2009/0096450 | A1* | 4/2009 | Roland | 324/315 |
| 2010/0013477 | A1* | 1/2010 | Morrell | 324/309 |
| 2010/0142823 | A1* | 6/2010 | Wang et al. | 382/195 |
| 2010/0237863 | A1* | 9/2010 | Stemmer | A61B 5/055 324/309 |
| 2011/0096092 | A1* | 4/2011 | Griswold et al. | 345/630 |
| 2011/0148410 | A1* | 6/2011 | Zaitsev | G01R 33/5611 324/309 |
| 2011/0254548 | A1* | 10/2011 | Setsompop et al. | 324/309 |

OTHER PUBLICATIONS

Breuer, Felix, et al. "Controlled aliasing in parallel imaging results in higher acceleration (CAIPIRINHA)." Proceedings of the 20th Annual Meeting of ESMRMB, Rotterdam, Netherlands. 2003.*

Pruessmann, Klaas P., et al. "SENSE: sensitivity encoding for fast MRI." Magnetic resonance in medicine 42.5 (1999): 952-962.*

International Search Report and Written Opinion under date of mailing of May 24, 2011 in connection with PCT/US2011/026250.

D.J. Larkman, et al.: "Use of Multicoil Arrays for Separation of Signal from Multiple Slices Simultaneously Excited"; Journal of Magnetic Resonance Imaging, vol. 13, No. 2, 2001; pp. 313-317; XP002636406.

W.E. Kyriakos et al.: "Generlaized encoding through the use of selective excitation in accelerated parallel MRI", NMR in Biomedicine, vol. 19, No. 3, May 2006; pp. 379-392; XP002546073.

F.A. Breuer et al.: Controlled Aliasing in Parallel Imaging Results in Higher Acceleration (CAIPIRINHA) for Multi-Slice Imaging, Magnetic Resonance in Medicine, vol. 53, pp. 684-691, 2005.

F.A. Breuer et al.: Controlled Aliasing in Volumetric Parallel Imaging (2D CAIPIRINHA), Magnetic Resonance in Medice, vol. 55, pp. 549-556, 2006.

J.A. de Zwart et al.: "Accelerated parallel imaging for functional imaging of the human brain", NMR in Biomedicine, vol. 19, pp. 342-351, 2006.

S.P. Souza et al.: "SIMA: Simultaneous Mulotislice Acquisiton of MR Images by Hadamard-Encoded Excitation", Journal of Computer Assisted Tomography, vol. 12, No. 6, pp. 1026-1030; 1988.

M.N.J. Paley et al.: "Simultaneous parallel inclined readout image technique", Magnetic Resonance Imaging, No. 24, pp. 557-562, 2006.

K. Teh et al.: "Parallel Imaging of Hyperpolarized Helium-32 with Simultaneous Slice Excitation", Magnetic Resonance in Medicine, vol. 55, pp. 258-262, 2006.

D.A. Feinberg et al.: "Multiplexed Echo Planar Imaging for Sub-Second Whole Brain FMRI and Fast Diffusion Imaging", PLoS ONE, vol. 5, No. 12, pp. 1-11, Dec. 2010.

* cited by examiner

METHOD FOR SIMULTANEOUS MULTI-SLICE MAGNETIC RESONANCE IMAGING USING SINGLE AND MULTIPLE CHANNEL RECEIVER COILS

CROSS-REFERENCE TO RELATED APPLICATIONS

This application represents the national stage entry of PCT International Application No. PCT/US2011/026250 filed Feb. 25, 2011, which claims the benefit of U.S. Provisional Patent Application Ser. No. 61/308,170, filed on Feb. 25, 2010, and entitled "Method for Simultaneous Multi-Slice Magnetic Resonance Imaging Using Single and Multiple Channel Receiver Coils", all of which are hereby incorporated herein by reference for all purposes.

STATEMENT REGARDING FEDERALLY SPONSORED RESEARCH

This invention was made with government support under EB007827 awarded by the National Institutes of Health. The government has certain rights in the invention.

BACKGROUND OF THE INVENTION

The field of the invention is magnetic resonance imaging ("MRI") methods and systems. More particularly, the invention relates to methods and systems for simultaneous multi-slice MRI, in which either a single or multiple channel receiver coil is employed to simultaneously acquire image data from multiple slice locations.

MRI uses the nuclear magnetic resonance ("NMR") phenomenon to produce images. When a substance such as human tissue is subjected to a uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped," into the x-y plane to produce a net transverse magnetic moment, $M_{xy}$. A signal is emitted by the excited nuclei or "spins," after the excitation signal $B_1$ is terminated, and this signal may be received and processed to form an image.

When utilizing these "MR" signals to produce images, magnetic field gradients ($G_x$, $G_y$, and $G_z$) are employed for the spatial encoding of the signals. Typically, the region to be imaged is scanned by a sequence of measurement cycles in which these gradients vary according to the particular localization method being used. The resulting set of received MR signals are digitized and processed to reconstruct the image using one of many well known reconstruction techniques.

The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically-proven pulse sequences and they also enable the development of new pulse sequences.

The MR signals acquired with an MRI system are signal samples of the subject of the examination in Fourier space, or what is often referred to in the art as "k-space." Each MR measurement cycle, or pulse sequence, typically samples a portion of k-space along a sampling trajectory characteristic of that pulse sequence. Most pulse sequences sample k-space in a raster scan-like pattern sometimes referred to as a "spin-warp," a "Fourier," a "rectilinear," or a "Cartesian" scan; however, other pulse sequences may sample k-space along non-Cartesian trajectories such as radial lines and spirals.

Depending on the technique used, many MR scans currently require many minutes to acquire the necessary data used to produce medical images. The reduction of this scan time is an important consideration, since reduced scan time increases patient throughout, improves patient comfort, and improves image quality by reducing motion artifacts. Many different strategies have been developed to shorten the scan time.

One such strategy for shortening scan time is referred to generally as "parallel MRI" ("pMRI"). Parallel MRI techniques use spatial information from arrays of radio frequency ("RF") receiver coils to substitute for the spatial encoding that would otherwise have to be obtained in a sequential fashion using RF pulses and magnetic field gradients, such as phase and frequency encoding gradients. Each of the spatially independent receiver coils of the array carries certain spatial information and has a different spatial sensitivity profile. This information is utilized in order to achieve a complete spatial encoding of the received MR signals, for example, by combining the simultaneously acquired data received from each of the separate coils. Parallel MRI techniques allow an undersampling of k-space by reducing the number of acquired phase-encoded k-space sampling lines, while keeping the maximal extent covered in k-space fixed. The combination of the separate MR signals produced by the separate receiver coils enables a reduction of the acquisition time required for an image, in comparison to a conventional k-space data acquisition, by a factor related to the number of the receiver coils. Thus the use of multiple receiver coils acts to multiply imaging speed, without increasing gradient switching rates or RF power.

Two categories of such parallel imaging techniques that have been developed and applied to in vivo imaging are so-called "image space methods" and "k-space methods." An exemplary image space method is known in the art as sensitivity encoding ("SENSE"), while an exemplary k-space method is known in the art as simultaneous acquisition of spatial harmonics ("SMASH"). With SENSE, the undersampled k-space data is first Fourier transformed to produce an aliased image from each coil, and then the aliased image signals are unfolded by a linear transformation of the superimposed pixel values. With SMASH, the omitted k-space lines are synthesized or reconstructed prior to Fourier transformation, by constructing a weighted combination of neighboring k-space lines acquired by the different receiver coils. SMASH requires that the spatial sensitivity of the coils be determined, and one way to do so is by "autocalibration" that entails the use of variable density k-space sampling.

A more recent advance to SMASH techniques using autocalibration is a technique known as generalized autocalibrating partially parallel acquisitions ("GRAPPA"), as described, for example, in U.S. Pat. No. 6,841,998. With GRAPPA, k-space lines near the center of k-space are sampled at the Nyquist frequency, in comparison to the undersampling employed in the peripheral regions of k-space. These center k-space lines are referred to as the so-called autocalibration signal ("ACS") lines, which are used to determine the weighting factors that are utilized to synthesize, or reconstruct, the missing k-space lines. In particular, a linear combination of individual coil data is used to create the missing lines of k-space. The coefficients for the combination are determined by fitting the acquired data to the more highly sampled data near the center of k-space.

Another strategy is to use so-called partial k-space echo-planar imaging ("EPI"), in which the number of acquired k-space lines is reduced and a relatively short echo time ("TE") is used, thereby minimizing signal dropout. The time required to cover k-space can be further reduced by the use of in-plane SENSE or one of its derivatives.

Other methods for decreasing scan time have been developed. For example, methods for the simultaneous acquisition of image data from multiple imaging slice locations, using an array of multiple radio frequency ("RF") receiver coils, and subsequent separation of the superimposed slices during image reconstruction have be introduced, as described by D. J. Larkman, et al., in "Use of Multicoil Arrays for Separation of Signal from Multiple Slices Simultaneously Excited," *Journal of Magnetic Resonance Imaging*, 2001; 13(2):313-317. This method is limited, however, in that the separation of the multiple slices is rendered difficult by the close spatial proximity of the aliased pixels that must be separated during image reconstruction. For example, if image data is acquired from three slices simultaneously, and with an inter-slice spacing of around 3 cm, then aliasing will be present along the slice-encoding direction, and this aliasing must be undone in order to produce reliable images. The origin of the aliased pixels are only 3 cm apart in space, and it is this spatial closeness of the aliased pixels that makes their separation difficult by standard parallel imaging methods, such as sensitivity encoding ("SENSE").

The difficulties of SENSE, and other similar methods, to properly separate the aliased pixels results from the differences in detection strength among the multiple array coil elements at the locations of the aliased pixels. In particular, the problem is that the detection profiles of the coil array elements are not unique enough on the spatial scale of a few centimeters. As a result, a high level of noise amplification, characterized by a high SENSE g-factor, is present in the separated images. This result is in contrast to the conventional implementation of SENSE methods, in which an undersampled phase encoding scheme produces aliasing along the phase-encoding direction, which is orthogonal to the slice-encoding direction. Moreover, this in-plane aliasing results in pairs of aliased pixels that are separated by one-half of the image field-of-view ("FOV"). For a conventional brain image, the FOV is equal to around 24 cm; thus, when aliasing occurs in the imaging plane, or slice, the distance between aliased pixels is around 12 cm. It is contemplated that it is the four-fold smaller distance between aliased pairs of pixels that results in significant noise amplification in the method disclosed by Larkman. It would therefore be desirable to provide a method for simultaneous multi-slice imaging that is produces less noise amplification than presently available methods, such as the one taught by Larkman.

Another notable method for simultaneous multi-slice imaging was described by D. A. Feinberg, et al., in "Simultaneous Echo Refocusing in EPI," *Magn. Reson. Med.*, 2002; 48(1):1-5. In this method, which is termed "SER-EPI," the RF excitation of the slices is sequential, as opposed to truly simultaneous. A readout gradient pulse is applied between two sequential excitations, and acts to shift the k-space data of one slice relative to the other along the $k_x$-direction, which corresponds to the readout direction in image space. By lengthening the readout window, the k-space data for both slices is captured sequentially. The data can then be cut apart and reconstructed separately. This approach has several downsides, however. Since the excitation is not simultaneous, the two slices do not have identical echo times ("TE"). In fact, the TEs typically differ by about 3 ms. This difference in TE is problematic, in that image intensity and contrast is exponentially dependent on TE. Thus, the two slices are not truly identical in image contrast or intensity. Another limitation of the SER-EPI method is that the lengthened readout needed to capture the shifted k-space data of the second slice increases the total readout duration. In turn, this increased duration increases the $B_0$ susceptibility distortions included in the resultant EPI images.

More recently, the SER-EPI method of Feinberg has been modified to include the approach utilized by Larkman, as described by D. A. Feinberg, et al., in "Multiplexed Echo Planar Imaging for Sub-Second Whole Brain fMRI and Fast Diffusion Imaging," PLos ONE (5):e15710. This more recently modified method, however, still includes the limitations of the reconstruction technique described by Larkman.

Simultaneous multi-slice methods have not gained much traction in conventional imaging since there are alternative parallel imaging methods, such as conventional SENSE and GRAPPA, for accelerating standard image acquisitions. However, as noted above, these methods do not confer the same acceleration benefits on pulse sequences such as EPI as they do on other conventional pulse sequences. Unlike parallel imaging methods such as SENSE and GRAPPA, multi-slice acquisition techniques do not aim to shorten the time spent on reading out k-space data, for example, by reducing the number of phase-encodings. Rather, they aim to acquire signal data from multiple image slice locations per acquisition, such that the number of repetitions of a pulse sequence can be reduced to similarly reduce overall scan time. For example, a three-fold accelerated multi-slice acquisition acquires image data from three image slice locations per each repetition of the EPI sequence. As a result of this simultaneous acquisition, the number of repetitions of an EPI sequence required to cover an imaging volume is reduced, thereby similarly reducing the total acquisition time.

It would therefore be desirable to provide a method for simultaneous, multi-slice imaging that allows for a more reliable separation of aliased pixels than currently available methods for simultaneous multi-slice imaging, so that the benefits associated with these techniques can be realized in a clinical setting. It would further desirable to provide such a method that would be amenable to functional MRI ("fMRI") techniques, including resting state or functional connectivity fMRI.

SUMMARY OF THE INVENTION

The present invention overcomes the aforementioned drawbacks by providing a method for reconstructing a plurality of images depicting a subject from image data that is simultaneously acquired from a corresponding plurality of slice locations with a magnetic resonance imaging ("MRI") system. Image data is acquired following the application of radio frequency ("RF") energy to the plurality of slice locations. The RF energy is tailored to provide a different phase to each of the plurality of slice locations. Reference image data is also acquired for each slice location following the application of RF energy that has the same phase as used to excite the respective slice location for the acquisition of the image data. Aliased images are reconstructed from the image data, and reference images are reconstructed from the reference image data. Using both of these image sets, an unaliased image is produced for each of the plurality of slice locations. Such a method is advantageous for performing functional MRI ("fMRI") and for acquiring a time series of image frames that covers the entire volume of the brain in a shorter period of time than is capable with previous methods. This advantageous benefit of the method makes it particularly well-suited for performing resting-state fMRI and for assessing functional connectivity. Thus, the herein provided method provides an advantageous imaging method for assessing the functional connectome with fMRI.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
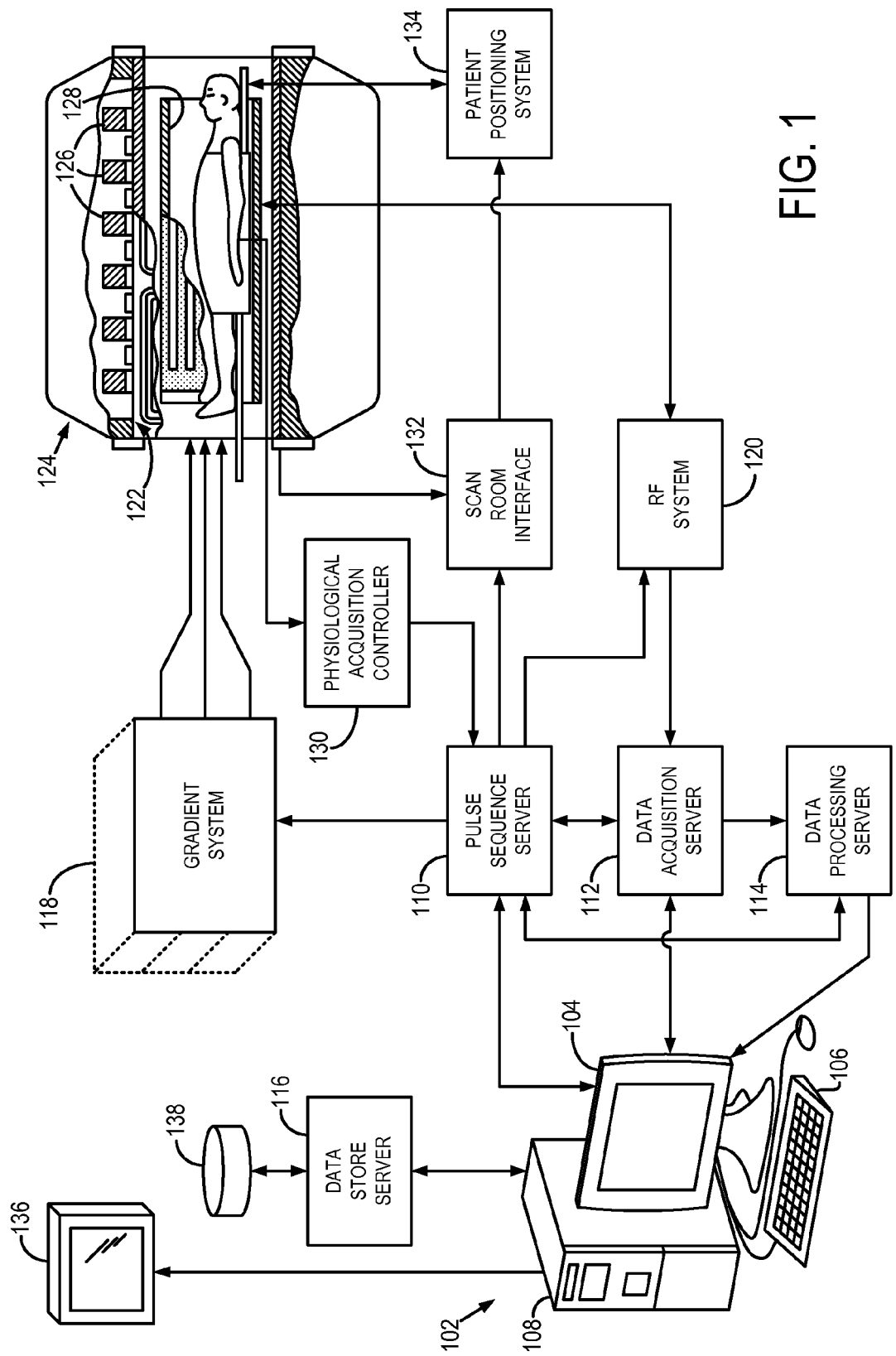
FIG. 1 is a block diagram of an exemplary magnetic resonance imaging ("MRI") system that employs the present invention.

Referring particularly now to FIG. 1, an exemplary magnetic resonance imaging ("MRI") system 100 is illustrated. The MRI system 100 includes a workstation 102 having a display 104 and a keyboard 106. The workstation 102 includes a processor 108, such as a commercially available programmable machine running a commercially available operating system. The workstation 102 provides the operator interface that enables scan prescriptions to be entered into the MRI system 100. The workstation 102 is coupled to four servers: a pulse sequence server 110; a data acquisition server 112; a data processing server 114, and a data store server 116.

The workstation 102 and each server 110, 112, 114 and 116 are connected to communicate with each other.

The pulse sequence server 110 functions in response to instructions downloaded from the workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 that includes a polarizing magnet 126 and a whole-body RF coil 128.

RF excitation waveforms are applied to the RF coil 128, or a separate local coil (not shown in FIG. 1), by the RF system 120 to perform the prescribed magnetic resonance pulse sequence. Responsive MR signals detected by the RF coil 128, or a separate local coil (not shown in FIG. 1), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays (not shown in FIG. 1).

The RF system 120 also includes one or more RF receiver channels. Each RF receiver channel includes an RF amplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2} \qquad (1);$$

and the phase of the received MR signal may also be determined:

$$\phi = \tan^{-1}\left(\frac{Q}{I}\right). \qquad (2)$$

The pulse sequence server 110 also optionally receives patient data from a physiological acquisition controller 130. The controller 130 receives signals from a number of different sensors connected to the patient, such as electrocardiograph ("ECG") signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. The data acquisition server 112 may also be employed to process MR signals used to detect the arrival of contrast agent in a magnetic resonance angiography ("MRA") scan. In all these examples, the data acquisition server 112 acquires MR data and processes it in real-time to produce information that is used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 are conveyed back to the workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

Figure 2:
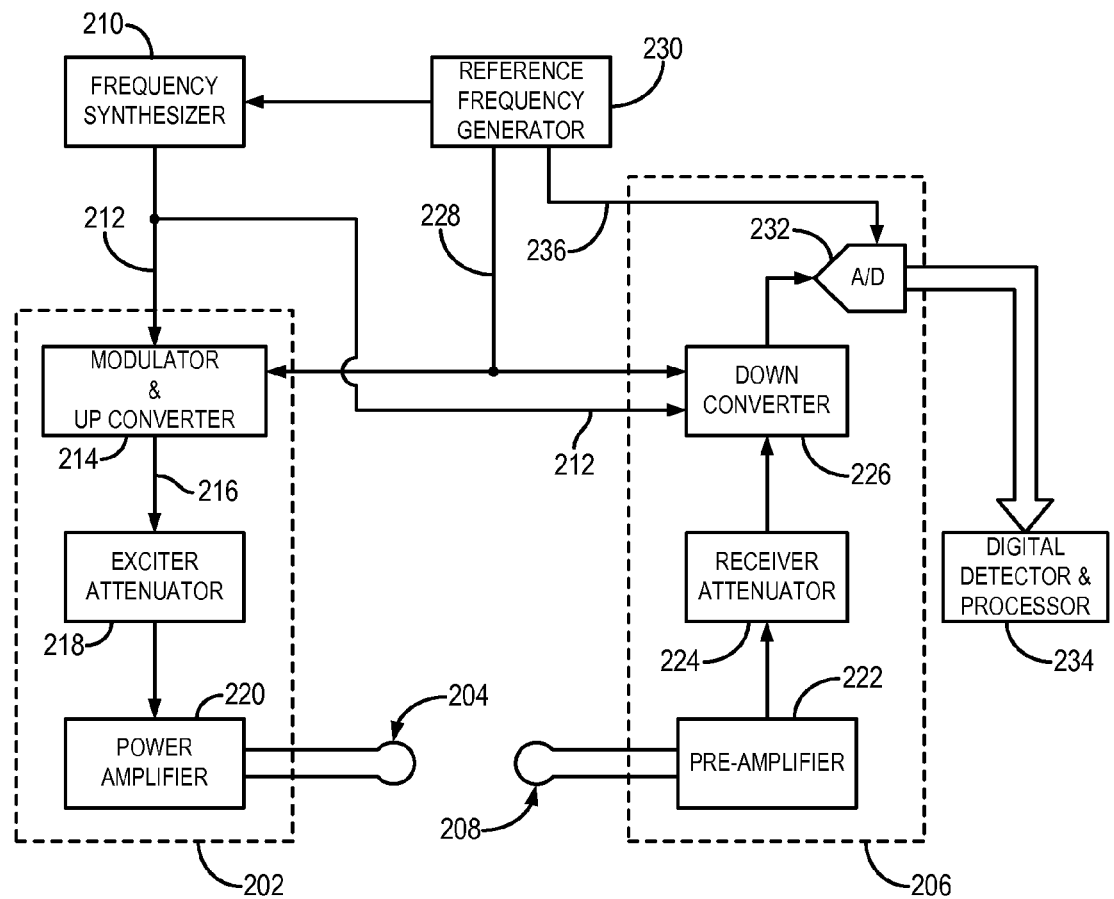
FIG. 2 is a block diagram of an exemplary radio frequency ("RF") system that forms part of a configuration of the MRI system of FIG. 1.

As shown in FIG. 1, the radiofrequency ("RF") system 120 may be connected to the whole body RF coil 128, or, as shown in FIG. 2, a transmission channel 202 of the RF system 120 may connect to a RF transmission coil 204 and a receiver channel 206 may connect to a separate RF receiver coil 208. Often, the transmission channel 202 is connected to the whole body RF coil 128 and each receiver section is connected to a separate local RF coil.

Referring particularly to FIG. 2, the RF system 120 includes a transmission channel 202 that produces a prescribed RF excitation field. The base, or carrier, frequency of this RF excitation field is produced under control of a frequency synthesizer 210 that receives a set of digital signals from the pulse sequence server 110. These digital signals indicate the frequency and phase of the RF carrier signal produced at an output 212. The RF carrier is applied to a modulator and up converter 214 where its amplitude is modulated in response to a signal, R(t), also received from the pulse sequence server 110. The signal, R(t), defines the envelope of the RF excitation pulse to be produced and is produced by sequentially reading out a series of stored digital values. These stored digital values may be changed to enable any desired RF pulse envelope to be produced.

The magnitude of the RF excitation pulse produced at output 216 is attenuated by an exciter attenuator circuit 218 that receives a digital command from the pulse sequence server 110. The attenuated RF excitation pulses are then applied to a power amplifier 220 that drives the RF transmission coil 204.

The MR signal produced by the subject is picked up by the RF receiver coil 208 and applied through a preamplifier 222 to the input of a receiver attenuator 224. The receiver attenuator 224 further amplifies the signal by an amount determined by a digital attenuation signal received from the pulse sequence server 110. The received signal is at or around the Larmor frequency, and this high frequency signal is down converted in a two step process by a down converter 226. The down converter 226 first mixes the MR signal with the carrier signal on line 212 and then mixes the resulting difference signal with a reference signal on line 228 that is produced by a reference frequency generator 230. The down converted MR signal is applied to the input of an analog-to-digital ("A/D") converter 232 that samples and digitizes the analog signal. The sampled and digitized signal is then applied to a digital detector and signal processor 234 that produces 16-bit in-phase (I) values and 16-bit quadrature (Q) values corresponding to the received signal. The resulting stream of digitized I and Q values of the received signal are output to the data acquisition server 112. In addition to generating the reference signal on line 228, the reference frequency generator 230 also generates a sampling signal on line 236 that is applied to the A/D converter 232.

Figure 3:
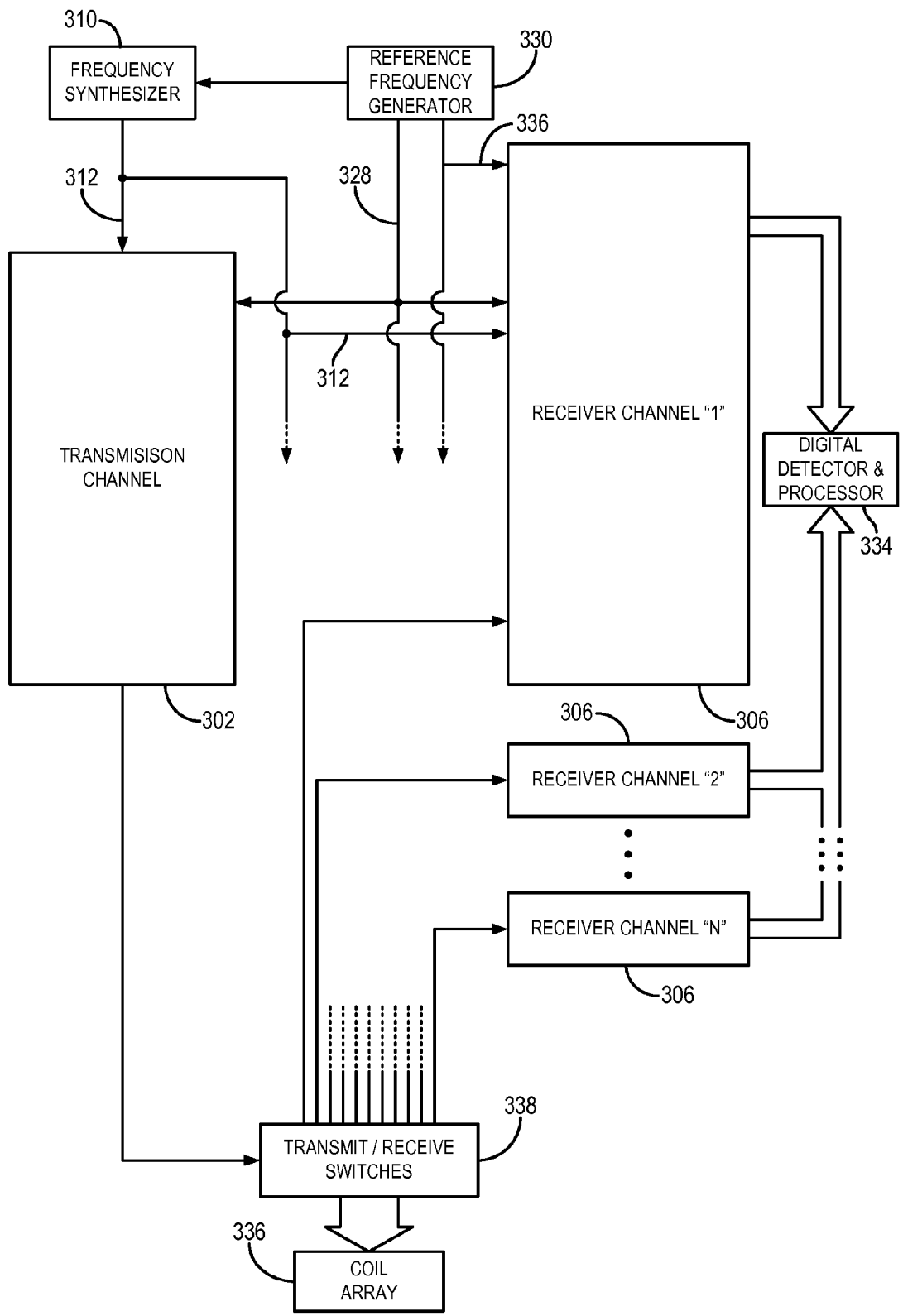
FIG. 3 is a block diagram of an exemplary RF system including a parallel receiver coil array that forms a part of another configuration of the MRI system of FIG. 1.

An alternative configuration of the RF system of FIG. 2 is shown in FIG. 3, to which reference is now made. In this alternative configuration, the RF transmission coil 204 and RF receiver coil 208 are replaced by a coil array 336, which includes at least one RF transmission coil and a plurality of receiver coils connected through one or more transmit/receive ("T/R") switches 338. The signal produced by the subject is picked up by the coil array 336 and applied to the inputs of a set of receiver channels 306. A pre-amplifier in each receiver channel 306 amplifies the signal by an amount determined by a digital attenuation signal received from the pulse sequence server 110. The received signal is at or around the Larmor frequency, and this high frequency signal is down converted in a two step process by a down converter. The down converter first mixes the MR signal with a carrier signal on line 312 and then mixes the resulting difference signal with a reference signal on line 328 that is produced by a reference frequency generator 330. The down converted MR signal is applied to the input of an analog-to-digital ("A/D") converter that samples and digitizes the analog signal. The sampled and digitized signal is then applied to a digital detector and signal processor 334 that produces 16-bit in-phase (I) values and 16-bit quadrature (Q) values corresponding to the received signal. The resulting stream of digitized I and Q values of the received signal are output to the data acquisition server 112. In addition to generating the reference signal on line 328, the reference frequency generator 330 also generates a sampling signal on line 336 that is applied to the A/D converter.

A method for accelerating the acquisition of a time course of images with a magnetic resonance imaging ("MRI") system by way of a simultaneous multi-slice data acquisition is provided. For example, the acquisition of image data with echo planar imaging ("EPI") or spiral imaging is accelerated by at least two-fold. Such a method is generally applicable to functional MRI ("fMRI"), resting-state fMRI ("R-fMRI"), arterial spin labeling ("ASL"), diffusion weighted image ("DWI"), and other situations where the acquisition of a large number of images are desirable. However, the method may advantageously improve the data acquisition efficiency for any number of other clinical applications, as will be appreciated by those skilled in the art.

In the method, groups of image slices, for example two or more slices, are simultaneously excited using a slice-selective tailored pulse that labels each slice by way of a unique radio frequency ("RF") phase. This method is generally referred to as "parallel slice phase tagging" ("PSPT"). Unraveling of the overlapping slices is accomplished using the RF phase labeling. It is noted that this method can be implemented using either a single channel, or multi-channel, receiver coil. Unraveling of the overlapping slices is further enhanced through the use of "reference slices." A set of reference slice images is obtained, for example, using the labeling phase assigned to each slice.

The PSPT method can be combined with SENSE acceleration, for significantly enhanced overall acceleration. This combination is generally referred to as "two-axis acceleration" ("TAC"), in which one axis is perpendicular to the slice, and the other axis is in the phase-encoding direction, for example. Cross-talk between slices is characterized and reduced by the tailored RF pulse formation and an appropriate slice separation algorithm. Additionally, increasing number of receiver channels in the coil array may reduce crosstalk between the slices. A time course of simultaneously excited slices can be easily registered using, for example, rigid-body as well as affine registration methods.

The method provided by the present invention allows for the acquisition of high-resolution functional connectivity data across the whole brain in a clinically reasonable time. Data can be obtained, for example, using R-fMRI with sufficiently thin slices such that intravoxel dephasing and signal drop-out are substantially mitigated. Data can be obtained within a repetition time ("TR") value of around two seconds, thereby preserving coherency of physiological fluctuations across the whole-brain data set. For EPI time-course methods, parallel acquisition allows a significantly enhanced tradeoff between temporal acceleration and increase of spatial resolution to the advance of neuroscience and diagnosis of human brain disease.

Figure 4:
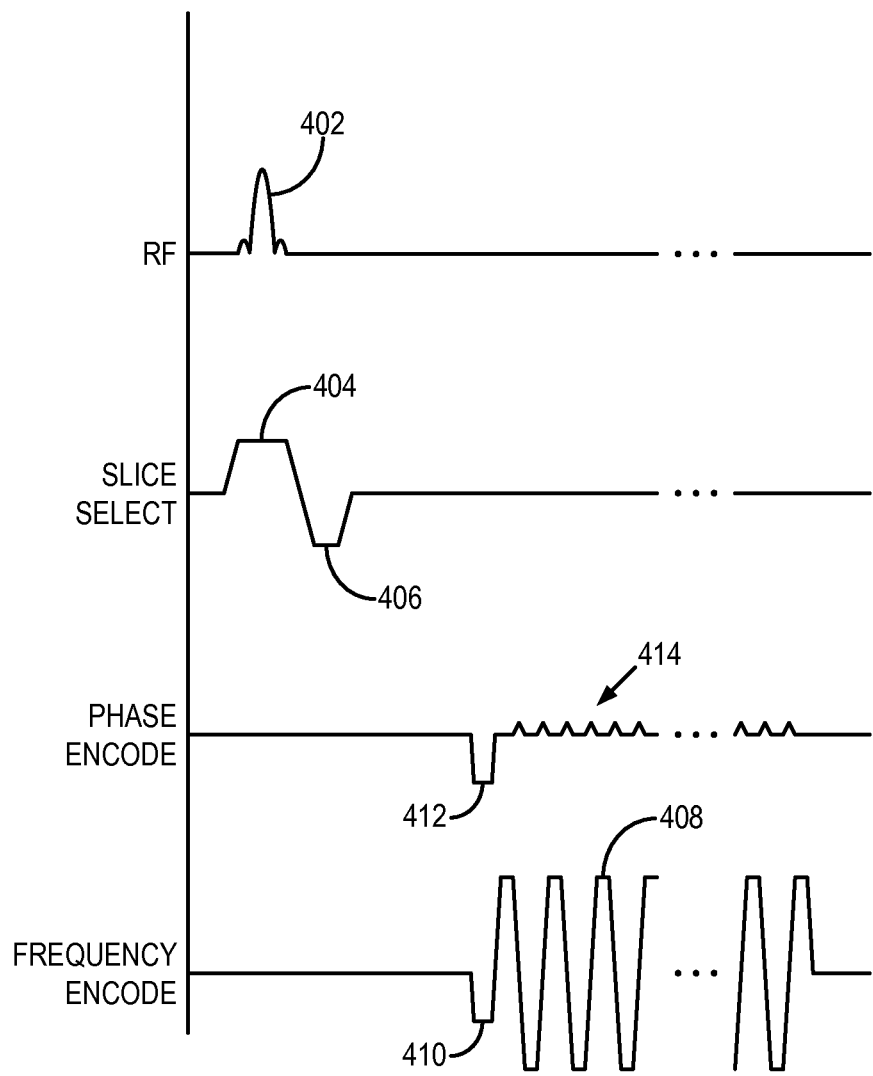
FIG. 4 is a pulse sequence diagram depicting an exemplary pulse sequence employed when practicing some embodiments of the present invention.

An exemplary pulse sequence employed to direct the MRI system to acquire image data simultaneously from multiple slice locations, in accordance with the present invention, is illustrated in FIG. 4. Such an exemplary pulse sequence is a gradient-recalled echo planar imaging ("EPI") pulse sequence. The pulse sequence includes a spatially selective radio frequency ("RF") excitation pulse 402 that is played out in the presence of a slice-selective gradient 404 in order to produce transverse magnetization in multiple prescribed imaging slices. The slice-selective gradient 404 includes a rephasing lobe 406 that acts to rephase unwanted phase dispersions introduced by the slice-selective gradient 404, such that signal losses resultant from these phase dispersions are mitigated.

Figure 5A:
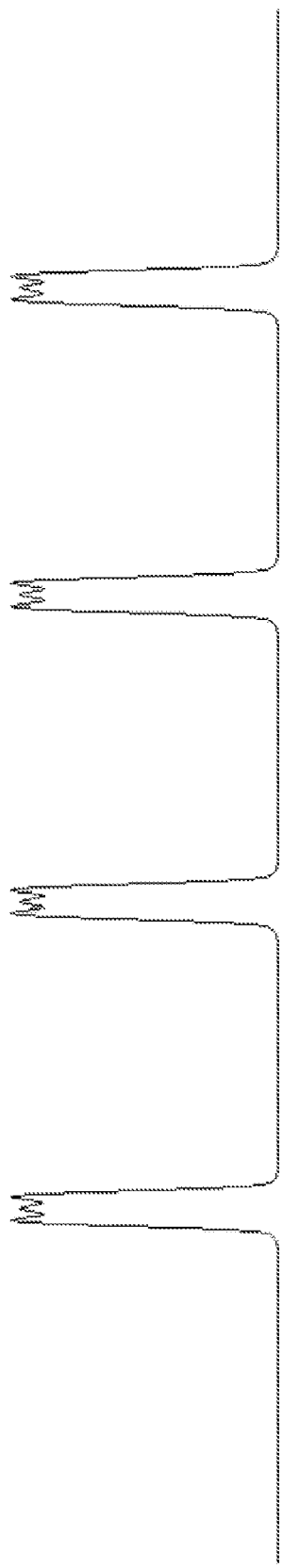
FIG. 5A is an exemplary set of four RF pulse profiles in frequency space.
Figure 5B:
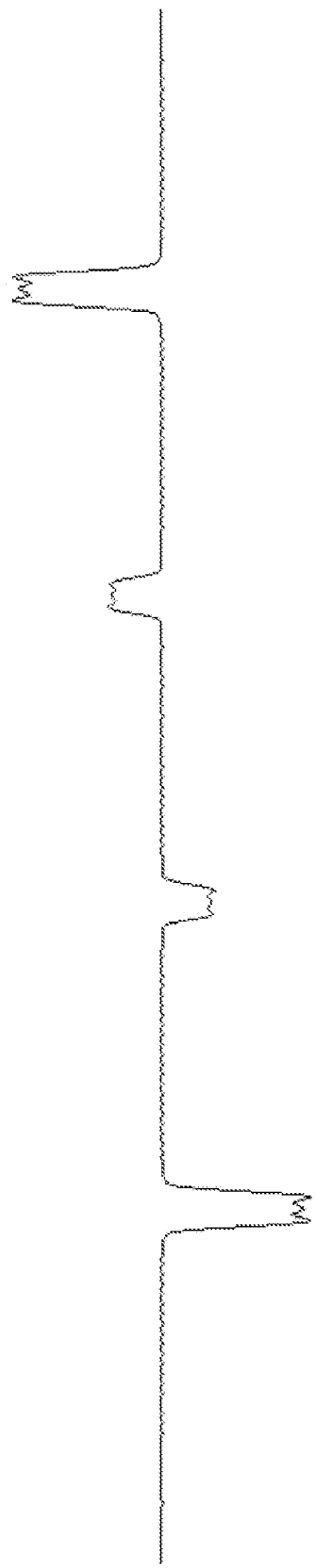
FIG. 5B is an exemplary set of four RF pulse phase profiles corresponding to the RF pulse profiles of FIG. 5A.
Figure 5C:
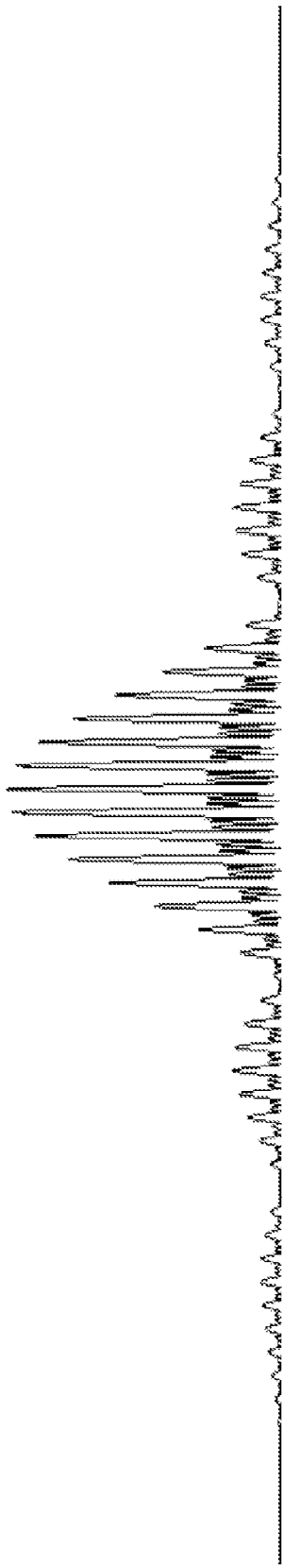
FIG. 5C is an exemplary composite RF pulse waveform produced by Fourier transforming and combining the RF pulse profiles of FIG. 5A.
Figure 5D:
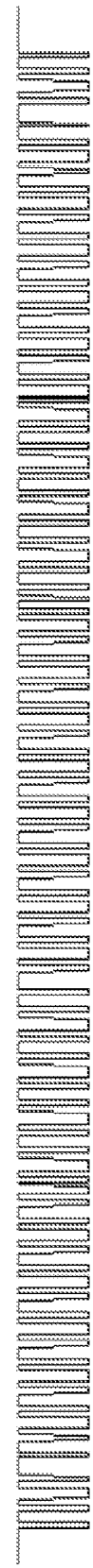
FIG. 5D is a phase of the composite RF pulse wave of FIG. 5C.

The RF excitation pulse 402 is, for example, a composite RF pulse that is tailored to simultaneously excite multiple slice locations, such that the transverse magnetization at each slice location is imparted a different phase. By way of example, and referring now to FIGS. 5A-5D, a desired slice profile is determined and the Fourier transform of that slice profile is calculated to determine the appropriate RF excitation pulse 402 profile, including the different phase information for the different slice locations. For example, the location and thickness for each desired slice location is selected and used to produce an RF pulse profile for each slice location in frequency space. Additionally, the tip angle of each RF pulse profile can be separately selected. Four such RF pulse profiles are shown in FIG. 5A, in which each different RF pulse profile has different frequency values and bandwidths associated with it, which correspond to the different spatial locations and slice thicknesses, respectively, that will be excited by the corresponding RF pulse. As shown in FIG. 5B, each RF pulse profile has a unique phase profile. In general, N such RF pulse profiles and N corresponding phase profiles are produced and then transformed to generate the desired RF pulse waveforms. By way of example, the Fourier transform of the RF pulse profiles in FIG. 5A produce four distinct RF pulse waveforms that, when combined, produce a composite RF pulse waveform, such as the one illustrated in FIG. 5C. The phase of the exemplary RF pulse waveform shown in FIG. 5C is illustrated in FIG. 5D. The composite RF pulse waveform may be obtained by summing the N RF pulse profiles and calculating the Fourier transform of the sum, or, alternatively, by adding the RF pulse waveforms produced by Fourier transforming each of the individual RF pulse profiles.

Exemplary phases for a four-slice acquisition include those lying in the first quadrant, that is: zero, thirty, sixty, and ninety degrees. It will be appreciated by those skilled in the art that any number of combinations of phase values may be readily implemented to phase-tag the respective slice locations, however. The individual RF pulses are also used to acquire reference image data, as will be described below. This reference image data, therefore, may be acquired with the same phases as those in the image data acquired following excitation by the composite RF pulse by using individual portions of the composite RF profile. It is noted that each complex-valued composite RF pulse may be formed from a single transmit frequency.

Referring again to FIG. 4, following excitation of the nuclear spins in the prescribed imaging slice, image data is acquired by sampling a series of gradient-recalled echo signals in the presence of an alternating readout gradient 408. The alternating readout gradient is preceded by the application of a pre-winding gradient 410 that acts to move the first sampling point along the frequency-encoding, or readout, direction by a prescribed distance in k-space. Spatial encoding of the echo signals along a phase-encoding direction is performed by a series of phase encoding gradient "blips" 412, which are each played out in between the successive signal readouts such that each echo signal is separately phase-encoded. The phase-encoding gradient blips 412 are preceded by the application of a pre-winding gradient 414 that acts to move the first sampling point along the phase-encoding direction by a prescribed distance in k-space. Together, the pre-winding gradients 410 and 414 act to begin the sampling of k-space at a prescribed k-space location. As is known in the art, the foregoing pulse sequence is repeated a plurality of times while applying a different slice-selective gradient 404 during each repetition such that a plurality of groups of multiple slice locations are sampled.

Figure 6A:
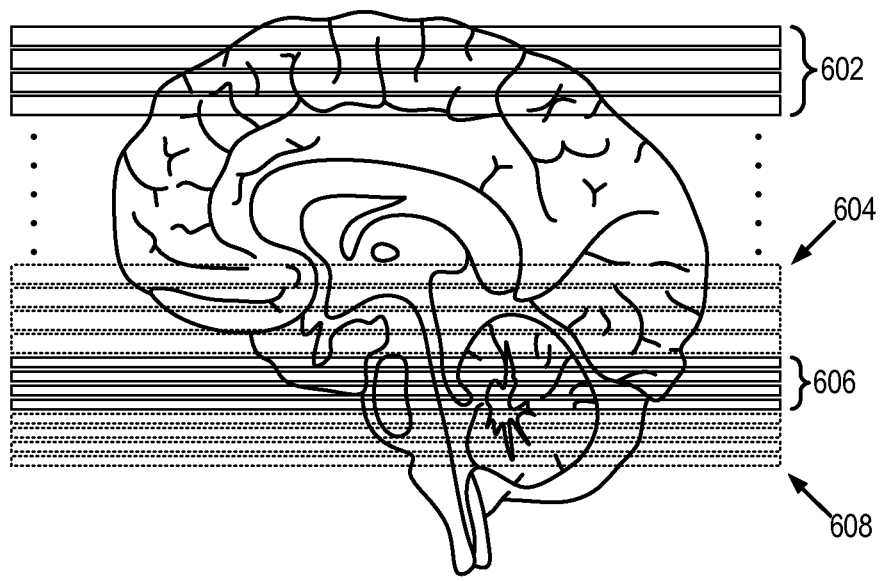
FIG. 6A is a pictorial representation of an exemplary data acquisition scheme using multiple slice locations that are simultaneously excited in accordance with some embodiments of the present invention.
Figure 6B:
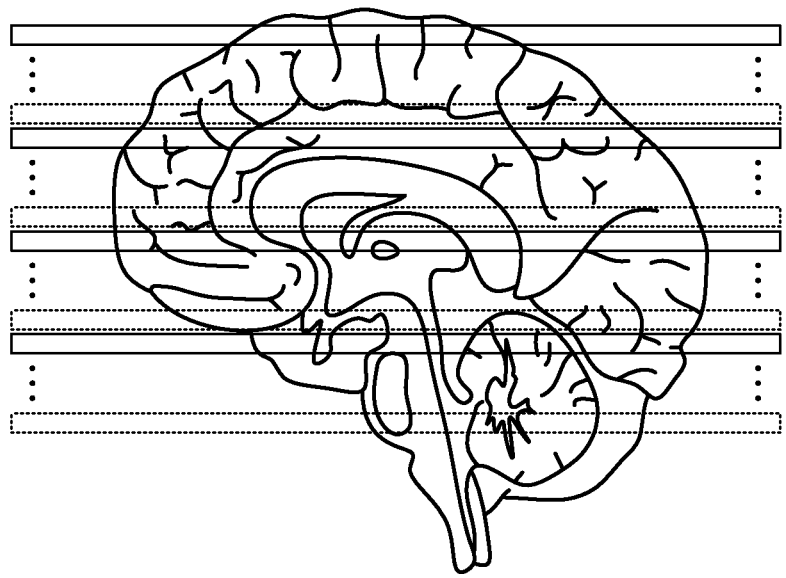
FIG. 6B is a pictorial representation of another exemplary data acquisition scheme using multiple slice locations that are simultaneously excited in accordance with some embodiments of the present invention.

With reference now to FIGS. 6A and 6B, exemplary groups of multiple slice locations are illustrated. In FIG. 6A, a first group of slice locations 602 is shown, in which the slice locations are closely grouped together. This close grouping of slice locations is moved sequentially through the desired field-of-view in order to acquire image data throughout the desired field-of-view. For example, the first group of slice locations is moved sequentially through a plurality of group locations until a last group location, indicated by dashed lines 604. When imaging in regions where significant air-tissue interfaces exist, such as the more inferior regions of the brain, it may be advantageous to use a thinner slice thickness than used for imaging other regions. Thus, as illustrated in FIG. 6A, a second group of slice locations 606 may be used, in which the slice locations are again closely spaced, but in which the slice thickness of each individual slice location in the group 606 is thinner than those in the first group 602. Like the first group 602, the second group of slice locations 606 may be sequentially moved through the field-of-view until a last group location 608 is reached. As shown in FIG. 6B, the selected slice locations do not need to be closely spaced; rather, each slice location in a group of slice locations may be spaced apart such that subsequent locations of the group of slice locations are interleaved with other group locations. It will be appreciated by those skilled in the art that the preceding examples of multiple slice location groupings and movement are just examples and that many other variations other than those expressly stated herein are possible within the scope of the invention.

When acquiring image data from multiple slice locations, it may be advantageous to use high dynamic range receivers that are well-suited for the increased signal associated with the simultaneous excitation of multiple slice locations. Exemplary high dynamic range receivers include, for example, EchoTek™ Series ECDR-GC316 digital receivers manufactured by Mercury Computer Systems, Inc. (Chelmsford, Mass.).

Figure 7:
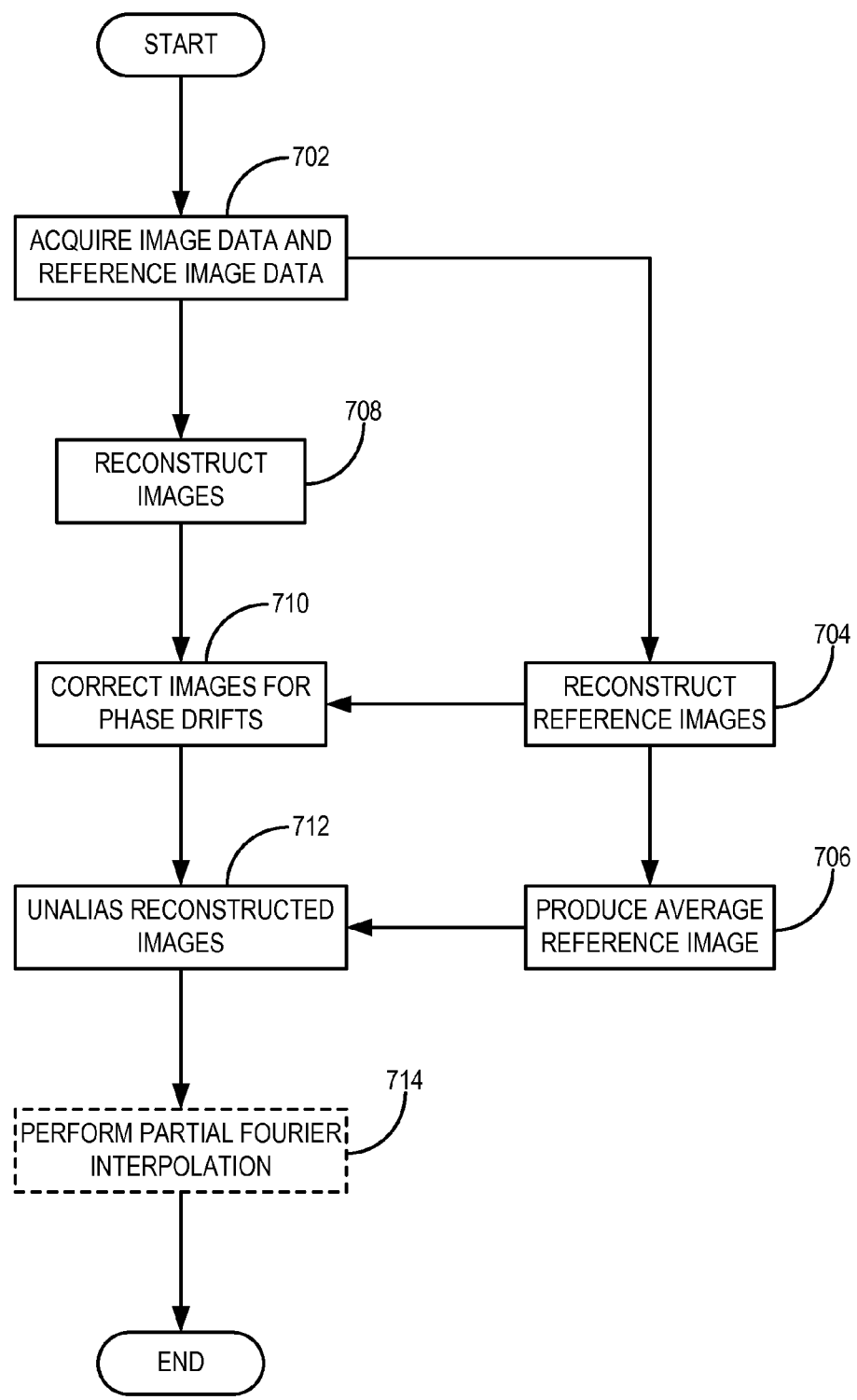
FIG. 7 is a flowchart setting forth the steps of an exemplary method for simultaneously acquiring image data from multiple slice locations and reconstructing images therefrom.

Referring now to FIG. 7, a flowchart setting forth the steps of an exemplary method for simultaneously acquiring image data from multiple slice locations and reconstructing images therefrom is illustrated. The method begins with the simultaneous acquisition of image data from multiple slice locations, as indicated at step 702. This image data may be acquired using, for example, the pulse sequence described above. The data acquisition step includes acquiring image data from a plurality of slice locations in groups of multiple slice locations that are acquired simultaneously. In addition, reference image data is acquired during data acquisition. Reference image data is acquired for each receiver coil and for each slice location. Thus, when a single receiver coil is employed, one reference image data set is acquired for each slice location, but when a multi-channel receiver coil array is employed, such as an n-channel receiver coil array, n reference image data sets are acquired for each slice location.

From the acquired reference image data, reference images are reconstructed, as indicated at step 704. These reference images are complex-valued images. In some instances, it may be advantageous to discard the first few reference images in a time course to avoid $T_1$ relaxation effects. These reconstructed reference images are then averaged to produce an average reference image having an improved signal-to-noise ratio ("SNR"), as indicated at step 706. For example, the reference images obtained at each slice location from each of the coils in the multi-channel receiver coil array are averaged together to produce an average reference image for that slice location. It is noted that, to some degree, physiological fluctuations may be averaged in this process. From the acquired image data, images are reconstructed, as indicated at step 708. Because image data was acquired from multiple slice locations simultaneously, these reconstructed images will include aliased signal information that is unaliased in later processes to produce the target images. Before unaliasing, it may be beneficial to remove unwanted phase drifts from the reconstructed images. It is contemplated that these unwanted RF phase drifts are associated with $B_0$ drifts, and may arise from a bulk susceptibility effect as the body of the subject relaxes toward a stable prone position, or from a heating effect during image acquisition. Thus, phase drifts are calculated and corrected for at step 710. This phase drift correction process is described in more detail below, and with respect to FIG. 8.

Referring still to FIG. 7, after the reconstructed images have been corrected for phase drifts, the images are unaliased to produce the target images, as indicated at step 712. In this process, each reconstructed image is unaliased into N images corresponding to the N slice locations simultaneously excited during data acquisition. In general, for each aliased voxel, a complex valued number exists from each of the n receiver channels, and, in addition, the reference images provide unaliased data from the N slices and n channels for that voxel. A system of equations is formed using this information, and may be solved, for example, by singular value decomposition to obtain the desired, unaliased image information. Data are combined across channels in this process, and the procedure is repeated across all voxels in each aliased image The herein described reconstruction method for parallel slice phase-tagging provides the reconstruction of either complex-valued or real-valued images. Complex-valued images preserve temporal phase variations from the reference images. Such phase variations are necessary if advanced statistical methods that require the use of complex-valued data are used, and half Fourier reconstruction additionally requires complex-valued images. However, if standard magnitude images are to be used in statistical analysis, only real-valued images need to be reconstructed.

The decision to reconstruct only real-valued images may yield an improvement in the unaliasing process. By solving for only the real component of the deviation from the reference images, the reconstruction process includes half of the number of unknowns with respect to reconstructing complex-valued images. Thus, the separation problem is more overdetermined when only real-valued solutions are desired, yielding an improvement in, for example, a least squares fitting of the separated image information. By reconstructing only real-valued images from the complex-valued phase-tagged image data, a reduction factor of two times the number of coils can be advantageously reached. This reduction is a twofold improvement over previously parallel imaging techniques.

As mentioned above, the reconstruction method utilizes reference images that may be acquired, for example, serially with the same pulse sequence used to acquire the multiple slice image data. These reference images contain spatially varying magnitude sensitivity from receiver coil profiles and spatially varying phase from the combined effects of the vector reception field for each specific RF receive channel, local magnetic field properties, and the RF excitation phase. Both the magnitude and phase of these reference images are utilized to separate the aliased images by solving, for example, the following system of equations:

$$\begin{pmatrix} S_{1,1}\cos(\theta_{1,1}) & -S_{1,1}\sin(\theta_{1,1}) & \cdots & -S_{1,N}\sin(\theta_{1,N}) \\ S_{1,1}\sin(\theta_{1,1}) & S_{1,1}\cos(\theta_{1,1}) & \cdots & S_{1,N}\cos(\theta_{1,N}) \\ \vdots & \vdots & \ddots & \vdots \\ S_{n,1}\sin(\theta_{n,1}) & S_{n,1}\cos(\theta_{n,1}) & \cdots & S_{n,N}\cos(\theta_{n,N}) \end{pmatrix} \begin{pmatrix} u_1 \\ \hat{u}_1 \\ \vdots \\ \hat{u}_N \end{pmatrix} = \begin{pmatrix} a_1 \\ \hat{a}_1 \\ \vdots \\ \hat{a}_n \end{pmatrix}; \quad (3)$$

where $a_n$ is the real component of the $n^{th}$ aliased signal; $\hat{a}_n$ is the imaginary component of the $n^{th}$ aliased signal; $u_N$ is the real component of the $N^{th}$ unaliased signal component, corresponding to the $N^{th}$ image slice location; $\hat{u}_N$ is the imaginary component of the $N^{th}$ unaliased signal component corresponding to the $N^{th}$ image slice location; $S_{n,N}$ is the magnitude of the reference image corresponding to the $N^{th}$ slice location and the $n^{th}$ receiver coil; and $\theta_{n,N}$ is the phase of the reference image corresponding to the $N^{th}$ slice location and the $n^{th}$ receiver coil. For simplicity, Eqn. (3) can be written as:

$$Su = a \quad (4);$$

where S is an encoding matrix containing the reference image magnitude, $S_{n,N}$, entries and the reference image phase, $\theta_{n,N}$, entries; u is an unaliased image matrix containing the real and imaginary components of the unaliased images, $u_N$ and $\hat{u}_N$, respectively; and a is an aliased image matrix containing the real and imaginary components of the aliased images, $a_n$ and $\hat{a}_n$, respectively.

By using the reference image magnitude and phase in Eqn. (3), the unaliased images have near unity values that can be scaled by a combination of the reference images to yield an expected spatial contrast. Generally, Eqn. (3) determines the deviation of the magnetization vector in the aliased images from the magnetization vector in the reference images. Optionally, standard partial Fourier interpolation can be performed on the separated images, as indicated at step 714. In the process for partial Fourier imaging, reference data and acquired data are zero filled and unaliased before performing partial Fourier interpolation.

For real-valued reconstructions, an assumption is made that the variation of the phase between the aliased images and reference images is negligible. With this assumption, the unaliased images are assumed to be real-valued, with phases defined entirely by the phases of the reference images. In this situation, Eqn. (3) may be rewritten as:

$$\begin{pmatrix} S_{1,1}\cos(\theta_{1,1}) & \ldots & S_{1,N}\cos(\theta_{1,N}) \\ S_{1,1}\sin(\theta_{1,1}) & \ldots & S_{1,N}\sin(\theta_{1,N}) \\ \vdots & \ddots & \vdots \\ S_{n,1}\sin(\theta_{n,1}) & \ldots & S_{n,N}\sin(\theta_{n,N}) \end{pmatrix} \begin{pmatrix} u_1 \\ \vdots \\ u_N \end{pmatrix} = \begin{pmatrix} a_1 \\ \hat{a}_1 \\ \vdots \\ \hat{a}_n \end{pmatrix}; \quad (5)$$

where the even columns of the encoding matrix, S, in Eqn. (3) and the even rows of the unaliased vector, u, in Eqn. (3) have been eliminated. Thus, when solving for a real-valued solution, the above system of equations includes 2n equations for N unknowns, as opposed to the 2n equations for 2N unknowns in Eqn. (3). As long as the number of receiver channels, n, is greater than or equal to twice the number of slice locations in each group of slice locations, that is, 2N, solutions to the real-valued parameterization exist. Through the assumption of real-valued unaliased images, and with the inclusion of the reference image phase in the encoding matrix, this parameterization allows higher accelerations than previously capable for parallel imaging. For example, accelerations up to 2n for coil arrays having n coils is possible.

For parallel imaging, the ratio of the signal-to-noise ratios of the separately acquired slices and unaliased slices yields the product of the unaliasing geometry-factor, or g-factor, g, and the square root of the reduction, or acceleration, factor, R:

$$g\sqrt{R} = \frac{SNR_{Ideal}}{SNR_{Unaliased}}. \quad (6)$$

With the described reconstruction method, the reduction factor is R=1 because the number of k-space lines is not reduced below the Nyquist criterion during acquisition from multiple slice locations. Thus, with the described reconstruction method, the ratio of SNRs of separately acquired to unaliased images is the g-factor:

$$g = \frac{SNR_{Ideal}}{SNR_{Unaliased}}. \quad (7)$$

The g-factor was initially described as a measure of coil covariance. With the addition of RF phase-tagging, it is expanded here to include the magnetization phase from RF excitation and magnetic field shimming. Furthermore, the g-factor can be reduced by increasing the overdetermined nature of the unaliasing problem by solving for only real-valued image values.

Figure 8:
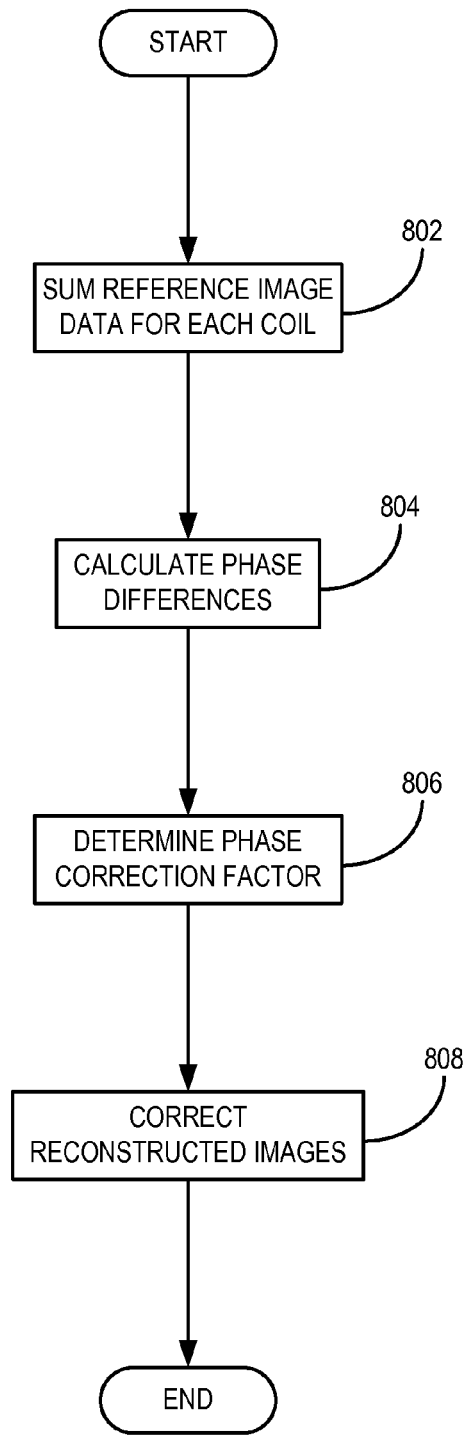
FIG. 8 is a flowchart setting forth the steps of an exemplary method for calculating and correcting phase drifts in reconstructed aliased images.

As described above, the reconstruction method may include the correction of the aliased images for phase drifts resulting from drifts in $B_0$, as well as for noise in the $G_x$ and $G_y$ gradients. Referring now to FIG. 8, a flowchart setting forth the steps of an exemplary method for calculating and correcting phase drifts in the reconstructed aliased images is illustrated. Generally, the method includes creating a facsimile of an aliased, multi-coil image data by summing the reference images and comparing the result with each aliased image to correct for phase drifts.

Thus, the phase drift correction method begins by summing the reference images, as indicated at step 802. Let the entries in an image time course be designated by:

$$A_m(k,l)e^{i\phi_m(k,l)} \quad (8);$$

where m counts images and k,l enumerates voxel locations x and y. Using this notation, the I, Q sum of the reference images over the n receiver channels for the $N^{th}$ slice location is given by:

$$A_0(k, l) = \sum_{j=1}^{n} A_{0,j}(k, l)e^{i\phi_{0,j}(k,l)}. \quad (9)$$

Using the calculated reference image sum, $A_0$, phase difference, $\Delta\phi_m$, between the reference image sum, $A_0$, and the aliased image for the $N^{th}$ slice location, $A_m$, are calculated, as indicated at step 804. This phase difference is represented as:

$$\Delta\phi_m(k,l)=\tan^{-1}(A_0(k,l)A_m(k,l)e^{i(\phi_m(k,l)-\phi_0(k,l))}) \quad (10).$$

As indicated at step 806, the next step in the phase drift correction method is to fit polynomials to the calculated phase difference, $\Delta\phi_m$. For example, the following fit is made:

$$\Phi_m(k, l) = a_0 + 2a_{1k}\left(\frac{k-\frac{R}{2}}{R}\right) + 2a_{2l}\left(\frac{l-\frac{R}{2}}{R}\right); \quad (11)$$

where R is the resolution of the image; $a_0$ corresponds to phase drifts arising from, at least in part, the transfer of heat produced in the gradient coils; and $a_{1k}$ and $a_{2l}$ correspond to phase drifts arising from noise in the gradient coils. The result of the fitting process is the calculation of a phase drift correction factor, $\Phi_m$, which is subtracted from the aliased images to correct for the phase drifts occurring therein, as indicated at step 808. This subtraction takes the form of:

$$I_m(k,l)=A_m(k,l)e^{i(\phi_m(k,l)-\Phi_m(k,l))} \quad (12);$$

where $I_m$ is the $m^{th}$ phase drift corrected, aliased image in a time course of images.

While the foregoing description focused primarily on application using a multi-channel receiver coil array, it will be appreciated by those skilled in the art that multiple slice acquisition can also be realized using a single receiver channel. For example, for two slices having a ninety degree phase difference between them, and assuming an ideal case in which each slice has a uniform phase profile and absolute phase aligned with the in-phase, I, acquisition channel, the first slice would be acquired in the I-channel and the second in the Q-channel. In such a case, twofold acceleration is attainable with a single RF coil.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for reconstructing a plurality of images depicting a subject from k-space data that is simultaneously acquired from a corresponding plurality of slice locations with a magnetic resonance imaging (MRI) system, the steps of the method comprising:
   a) simultaneously acquiring k-space data from a plurality of slice locations with the MRI system following application of radio frequency (RF) energy to the plurality of slice locations, the RF energy applying a different phase to each of the plurality of slice locations;
   b) acquiring reference k-space data from one of the plurality of slice locations with the MRI system following application of RF energy to the one of the plurality of slice locations, the RF energy applying a phase to the one of the plurality of slice locations corresponding to the different phase applied to the corresponding slice location in step a);
   c) repeating step b) for each of the different phases of the RF energy applied in step a) to acquire reference k-space data for each of the plurality of slice locations;
   d) reconstructing aliased images from the k-space data acquired in step a);
   e) reconstructing reference images from the reference k-space data acquired in steps b) and c), wherein each reference image is a complex-valued image that depicts the subject; and
   f) producing an unaliased image for each of the plurality of slice locations using the aliased images reconstructed in step d) and the reference images reconstructed in step e).

2. The method as recited in claim 1 in which step f) includes solving a system of equations that relates a magnitude of the reference images, a phase of the reference images, and the aliased images to each of the unaliased images.

3. The method as recited in claim 2 in which solving the system of equations in step f) includes using a least squares estimation.

4. The method as recited in claim 2 in which solving the system of equations in step f) includes using an encoding matrix having entries that are a product between the magnitude each of the reference images and at least one of a sine and a cosine of the phase of the same one of the reference images.

5. The method as recited in claim 1 in which step f) includes correcting the aliased images for phase drifts before producing the unaliased images.

6. The method as recited in claim 1 in which the k-space data acquired in step a) is a time course of k-space data.

7. The method as recited in claim 6 in which the time course of k-space data is functional image data representative of neuronal activity occurring in the subject during the acquisition of the image data in step a).

8. The method as recited in claim 1 in which the k-space data acquired in step a) is acquired with a multiple channel receiver coil array, the reference data acquired in step b) is acquired for one of the multiple channels in the multiple channel receiver coil array, and step c) includes repeating step b) for each channel in the multiple channel receiver coil array before repeating step b) for each of the plurality of slice locations.

9. The method as recited in claim 8 in which step f) includes solving a system of equations that relates a magnitude of the reference images, a phase of the reference images, and the aliased images to each of the unaliased images.

10. The method as recited in claim 9 in which step f) includes producing an average reference image for each slice location by averaging respective ones of the reference images corresponding to reference k-space data acquired from the respective slice location by each of the different coils in the multiple channel receiver coil array.

11. The method as recited in claim 10 in which the system of equations includes an encoding matrix having entries that are a product between the magnitude each of the average reference images and at least one of a sine and a cosine of the phase of the same one of the average reference images.

12. The method as recited in claim 8 in which step f) includes:
   i) summing respective ones of the reference images corresponding to reference k-space data acquired from different coils in the multiple channel receiver coil array for a given slice location;
   ii) calculating a phase difference between the summed reference image produced in step f)i) and the aliased image corresponding to the given slice location;
   iii) determining a phase correction factor using the calculated phase difference; and
   iv) applying the phase correction factor to the corresponding aliased image.

13. The method as recited in claim 12 in which step f)iii) includes fitting the calculated phase difference to a polynomial that includes terms that relate to phase drifts arising from noise and from heat transfer in gradient coils that form a part of the MRI system.

14. The method as recited in claim 1 in which the RF energy applied in step a) is tailored by performing a Fourier transform on a desired slice profile that defines a location and a phase for each of the plurality of slice locations.

15. The method as recited in claim 1 further comprising:
   g) performing a spin conditioning pulse sequence before acquiring k-space data in step a).

16. The method as recited in claim 15 in which the spin conditioning pulse sequence performed in step g) provides at least one of fat suppression and diffusion weighting.

17. The method as recited in claim 1 in which the k-space data acquired in step a) is undersampled k-space data and step f) includes producing the unaliased images using a reconstruction technique that accounts for a partial sample of k-space.

18. The method as recited in claim 17 in which the reconstruction technique that accounts for partial sampling of k-space includes at least one of SENSE and GRAPPA.

19. The method as recited in claim 1 in which the k-space data acquired in step a) is acquired during a period of time such that the k-space data represents a time course of image frames, and step f) includes reconstructing a plurality of image frames for each of the plurality of slice locations, the plurality of image frames for each of the plurality of slice locations thereby forming a time series of images for the respective one of the plurality of slice locations.

20. The method as recited in claim 1 in which the subject is a brain and plurality of slice locations substantially cover an entire volume of the brain.

21. The method as recited in claim 1 further comprising selecting a thickness of each of the plurality of slice locations before acquiring the k-space data in step a).

* * * * *